United States Patent [19]
Sandrin et al.

[11] Patent Number: 5,821,117
[45] Date of Patent: Oct. 13, 1998

[54] XENOTRANSPLANTATION THERAPIES

[75] Inventors: Mauro S. Sandrin, Brunswick; Ian F. C. McKenzie, West Brunswick, both of Australia

[73] Assignee: The Austin Research Institute, Heidelberg, Australia

[21] Appl. No.: 214,580

[22] Filed: Mar. 15, 1994

[30] Foreign Application Priority Data

Mar. 16, 1993 [AU] Australia ................................ PL 7854

[51] Int. Cl.$^6$ .............................. C12N 15/63; C12N 5/10; C12N 15/54
[52] U.S. Cl. ........................ 435/320.1; 435/325; 536/23.2
[58] Field of Search .............................. 435/240.2, 172.3, 435/320.1, 325; 536/23.1, 23.2

[56] References Cited

FOREIGN PATENT DOCUMENTS

WO91/12340  8/1991  WIPO.
WO93/16729  9/1993  WIPO.

OTHER PUBLICATIONS

Archer, F. J., *Diabetologia*, 24:185–190, 1983.
Blanchard, et al., *Xeno*, 3;68–71, 1995.
Brinster et al., *Proc. Natl. Acad. Sci. USA*, 86:7087–7091, 1989.
Galili et al., *J. Biol. Chem.*, 263:17755–17762, 1988.
Groth et al., *Transplantation Proceedings*, 24:972–973, 1992.
Groth et al., *Transplantation Proceedings*, 25:970, 1993.
Hesse et al., *Transplantation Proceedings*, 24:1016–1017, 1992.
Henretta et al., *Transplantation Proceedings*, 25:412–4131, 1993.
Kearns–Jonker, et al., *Transplantation*, 63:588–593, 1997.
Korsgren et al., *Transplantation*, 45:509–514, 1988.
LaVecchio et al., *Transplantation*, 60:841–847, 1995.
Marchetti, et al., *Transplantation Proceedings*, 24:637, 1992.
McCullagh, P., *The Foetus as Transplant Donor*, John Wiley & Sons, New York, 91, 1987.
Osorio et al., *Transplantation Proceedings*, 25:968–969, 1993.
Parisius et al., U.S. Patent No. 4,797,213, Jan. 10, 1989.
Pittman et al., *Transplantation Proceedings*, 25:986–987, 1993.
Platt, et al., *Immunology Today*, 11:450–457, 1990.
Ratner, et al., *Transplantation Proceedings*, 24:583–585, 1992.
Reemtsma, K., *Transplantation Proceedings*, 2:513–515, 1970.
Ricordi et al., *Surgery*, 107:688–694, 1990.
Rosenberg, U.S. Patent No. 4,332,893. Jun. 1, 1982.
Scharp et al., U.S. Patent No. 4,868,121. Sep. 19, 1989.
Smithies et al., *Nature*, 317:230–234, 1985.
Sun et al., *ASAIO Journal*, Biohybrid Organs Symposium Part II, 125–127, 1992.
Tze et al., *Transplantation Proceedings*, 21:2736–2738, 1989.
Weber et al., *Transplantation Proceedings*, 25:462–463, 1993.
Welsh et al. *Biomed. Biochim. Acta*, 49;1157–1164, 1990.
Wilson et al., *Diabetes*, 38:Supp.1:217–219, 1989.
Yamaguchi et al, *Transplantation Proceedings*, 24:1010–1012, 1992.
Yoneda et al., *Diabetes*, 38:213–216, 1989.
Sandrin et al. Enzymatic remodelling of the carbohydrate surface of a xenogenic cell substantially reduces human antibody binding and complement–mediated cytolosis. Nature Medicine vol. 1, pp. 1261–1267, 1995.
Capecchi M R, "Altering the Genome by Homologous Recombination," *Science* 244:1288–1292, 1989.
Capecchi M R, "The New Mouse Genetics: Altering the Genome by Gene Targeting," *Trends in Genetics* 5:70–76, 1989.
Cooper et al, "Specific Intravenous Carbohydrate Therapy: A New Approach to the Inhibition of Antibody–Mediated Rejection Following ABO–Incompatible Allografting and Discordant Xenografting," *Transplant Proceedings* 25:377–378, 1993.
Cosgrove et al, "Mice Lacking MHC Class II Molecules," *Cell* 66:1051–1066, 1991.
Dabkowski et al, "Characterisation of the Pig $\alpha(1–3)$ Galactose Transferase—Implications for Xenotransplantation," *Transplant Proceedings* 25:2921, 1993.
Dalmasso et al, "Mechanism of Complement Activation in the Hyperacute Rejection of Porcine Organs Transplanted into Primate Recipients," *Am J Pathology* 140:1157–1166, 1992.
Galili et al, "Human Natural Anti–$\alpha$–Galactosyl IgG: II. The Specific Recognition of $\alpha(1\rightarrow3)$–linked Galactose Residues," *J Exp Med* 162:573–582, 1985.
Galili et al, "Evolutionary relationship between the natural anti–Gal antibody and the Gal$\alpha1\rightarrow3$Gal epitope in primates," *Proc Natl Acad Sci, USA* 84:1369–1373, 1987.
Galili et al, "Man, Apes and Old World Monkey Differ from Other Mammals in the Expression of $\alpha$–Galactosyl Epitopes on Nucleated Cells," *J Biol Chem* 263:17755–17762, 1988.
Galili et al, "Gene sequences suggest inactivation of $\alpha$–1, 3–galactosyltransferase in catarrhines after the divergence of apes from monkeys," *Proc Natl Acad Sci, USA* 88:7401–7404, 1991.

(List continued on next page.)

*Primary Examiner*—James Ketter
*Assistant Examiner*—John S. Brusca
*Attorney, Agent, or Firm*—Maurice M. Klee; Seth A. Fidel

[57] ABSTRACT

DNA sequences encoding a porcine Gal$\alpha(1,3)$ galactosyl transferase and clones containing such sequences are provided. The porcine Gal$\alpha(1,3)$ galactosyl transferase produces the Gal$\alpha(1,3)$Gal epitope on the surfaces of porcine cells. This epitope is recognized by human anti-Gal$\alpha(1,3)$ Gal antibodies which are responsible for hyperacute rejection of xenotransplanted pig cells, tissues and organs.

8 Claims, 7 Drawing Sheets

OTHER PUBLICATIONS

Holgersson et al, "Carbohydrate Specificity of Human Immunoglobulin–M Antibodies With Pig Lymphocytotoxic Activity," *Transplant Proceedings* 24:605–608, 1992.

Joziasse et al, "Bovine α1→3–Galactosyltransferase: Isolation and Characterization of a cDNA Clone," *Journal of Biological Chemistry* 264:14290–14297, 1989.

Larsen et al, "Isolation of a cDNA encoding a murine UDPgalactose:β–D–galactosyl–1,4–N–acetyl–D–glucosaminide α–1,3–galactosyltransferase: Expression cloning by gene transfer," *Proc Natl Acad Sci, USA* 86:8227–8231, 1989.

Merlino G T, "Transgenic Animals in Biomedical Research," *FASEB J* 5:2996–3001, 1991.

Platt et al, "Endothelial Cell Antigens Recognized by Xenoreactive Human Natural Antibodies," *Transplantation* 50:817–822, 1990.

Sandrin et al, "Isolation and Characterization of cDNA Clones for Mouse Ly–9," *J Immunol* 149:1636–1641, 1992.

Sandrin et al, "Studies on Human Naturally Occurring Antibodies to Pig Xenoantigens," *Transplant Proc* 25:2917–2918, 1993.

Sandrin et al, "Anti–pig IgM antibodies in human serum react predominantly with Gal (α1–3) Gal epitopes," *Proc Natl Acad Sci, USA* 90:11391–11395, 1993.

Vaughan et al, "Biochemical Analysis of the Major Pig Xenoantigens Recognised by Humans," *Transplant Proc* 25:2919–2920, 1993.

Yang et al, "Xenoantigens Expressed on Swine Erythrocytes, Lymphoblastoid Cells and Endothelial Cells," *Transplant Proc* 24:593–594, 1992.

Zijlstra et al, "Germ–line Transmission of a disrupted β2–microglobulin gene produced by homologous recombination in embryonic stem cells," *Nature* 342:435–438, 1989.

XENOTRANSPLANTATION THERAPIES

This invention relates to xenotransplantation (transplantation across species) and is particularly concerned with methods of alleviating xenotransplant rejection, maintenance of xenotransplanted tissue in an animal, nucleotide sequences useful in xenotransplant therapies, rejection resistant transgenic organs, and transgenic animals whose tissues are rejection-resistant on xenotransplantation.

The current shortage of tissues for human transplantation has led to recent close examination of xenografts as a possible source of organs. However, when tissues from non human-species are grafted to humans, hyperacute rejection occurs due to the existence of natural antibodies in human serum which react with antigens present in these species, with rejection occurring within 10–15 minutes of transplantation. This phenomenon depends, in general, on the presence of some or all of antibody, complement, neutrophils, platelets and other mediators of inflammation. In transplantation of vascularized organs between "discordant" species (those in which natural antibodies occur) the first cells to encounter natural antibodies are the endothelial cells lining the blood vessels and it is likely that activation of these cells is induced by antibody binding to xenoantigens or other factors, leading to hyperacute rejection.

There is considerable uncertainty in the art concerning the nature of possible target xenoantigens on xenograft tissues. Platt et al (Transplantation 50:817–822, 1990) and Yang et al (Transplant. Proc. 24:593–594, 1992) have identified a triad of glycoproteins of varying molecular weights as the major targets on the surface of pig endothelial cells. Other investigators (Holgersson et al, Transplant Proc 24:605–608, 1992) indicate glycolipids as key xenoantigens.

We have now found that xenograft rejection, particularly in the context of pig tissue, is associated with antibodies reactive with galactose in an $\alpha(1,3)$ linkage with galactose, (the Gal$\alpha$(1,3)Gal epitope) Modulating the interaction between antibodies reactive with the Gal$\alpha$(1,3)Gal epitope of xenotransplant tissue effects rejection.

In accordance with the first aspect of this invention, there is provided a method of inhibiting xenotransplant rejection in an animal patient, comprising administering to the patient an effective amount of an antagonist of antibody binding to xenotransplant antigens having galactose in an $\alpha(1,3)$ linkage with galactose.

Another aspect of this invention relates to the maintenance of xenograft tissue in an animal, which comprises administering to the animal a graft rejection effective amount of an antagonist to antibodies which bind to the xenograft antigen epitope Gal$\alpha$(1,3)Gal.

In another aspect of this invention there is provided a method of inhibiting the binding of antibodies to the Gal$\alpha$(1,3)Gal epitope which comprises modulating the interaction between the antibodies and the epitope with an antagonist which blocks the binding of the antibodies to the Gal$\alpha$(1,3)Gal epitope.

Preferably the xenograft recipient is a human. Age is not a determining factor for xenograft transplantation although transplants in the elderly over 75 years would normally not be carried out. The invention is directed particularly to human transplantation with xenograft tissue.

Xenografted tissue is preferably of pig origin. Tissues from other mammals are also contemplated for use in this invention. Preferably the xenotransplanted tissue is in the form of an organ, for example, kidney, heart, lung or liver. Xenotransplant tissue may also be in the form of parts of organs, cell clusters, glands and the like. Examples include lenses, pancreatic islet cells, skin and corneal tissue. The nature of the xenotransplanted tissue is not of itself critical as any xenotransplanted tissue which expresses antigens having Gal$\alpha$(1,3)Gal epitopes may be utilized in accordance with this invention.

The binding of antibody to the Gal$\alpha$(1,3)Gal epitope expressed on xenotransplanted tissue provokes rejection of the tissue by humoral as well as cell-mediated immune effects leading to tissue rejection in a very short time scale, such as less than one hour. Antagonists which antagonize the binding of antibodies to the Gal$\alpha$(1,3)Gal epitope block antibody binding and therefore inhibit xenotransplant rejection. Because antibody binding is blocked, immune responses which give rise to tissue rejection are prevented.

In accordance with a further aspect of this invention, there is provided an antagonist which modulates the interaction of antibodies directed against Gal$\alpha$(1,3)Gal.

Any antagonist capable of modulating the interaction between antibodies directed to the Gal$\alpha$(1,3)Gal linkage may be utilized in this invention. By reference to modulation, is meant blockage of antibody binding or decrease in affinity reactivity of antibodies for the Gal$\alpha$(1,3)Gal epitope. Various mechanisms may be associated with the blockage of antibody binding or decreased affinity of antibodies for their respective epitope. These include binding or association with the antibody reactive site and change of conformation of the antibody reactive site, such as by binding to residues associated with, adjacent to, or distanced from the active site, which effect the conformation of the active site such that it is incapable of binding the Gal$\alpha$(1,3)Gal epitope or binds the epitope with reduced affinity. For example, in accordance with techniques well known in the art (see, for example, Coligan, et al., eds. *Current Protocols In Immunology*, John Wiley & Sons, New York, 1992; Harlow and Lane, *Antibodies, A Laboratory Manual*, Cold Spring Harbor Laboratory, New York, 1988; and Liddell and Cryer, *A Practical Guide To Monoclonal Antibodies*, John Wiley & Sons, Chichester, West Sussex, England, 1991), such a change of the conformation of the antibody reactive site can be achieved through the use of an anti-idiotypic antibody raised against the natural antibody or fragments thereof. As is also well known in the art, these anti-idiotypic antibodies may be modified to enhance their clinical usefulness, for example by enzymatic techniques such as preparing Fab' fragments, or by recombinant techniques such as preparing chimeric, humanized, or single chain antibodies.

This invention is not limited to any specific antagonist and any antagonist which is non-toxic and which modulates the interaction between antibodies specific for the Gal$\alpha$(1,3)Gal epitope may be used in this invention. Suitable examples of antagonists include D-galactose and melibiose, stachyose and methyl-$\alpha$-D-galactopyranoside, D-galactosamine and derivatives thereof. The term derivatives encompasses, for example, any alkyl, alkoxy, alkylkoxy, aralkyl amine, hydroxyl, nitro, heterocycle, sulphate and/or cycloalkyl substituents whether taken alone or in combination, which derivatives have antagonist activities. This may be assessed according to methods as herein described. Carbohydrate polymers containing one or more of the aforesaid carbohydrate moieties or derivatives may also be utilized in this invention.

The amount of antagonists which is effective to modulate interaction between antibodies reactive with Gal$\alpha$(1,3)Gal epitopes will vary depending upon a number of factors. These include the nature of the animal being treated, the nature of species of the transplanted tissue, the physical condition of the transplant recipient (age, weight, sex and health) and the like. In respect of human transplant recipients of tissue, for example from pigs, the amount of antagonists administered will generally depend upon the judgement of a consulting physician. As an example, a graft rejection effective amount of an antagonist in human subjects may be in the order of from 0.01 mg to 1000 gm per dose, more preferably 10 mg to 500 mg, more preferably 50 mg to 300 mg, and still more preferably 50 mg to 200 mg per dose.

The schedule of administration of antagonists to inhibit rejection and maintain xenografts will depend upon varying factors as mentioned above. Varying dosage regimes may be contemplated, such as daily, weekly, monthly or the like.

The mode of administration of antagonists and dosage forms thereof are not critical to this invention. Antagonists may be administered parenterally (intravenous, intramuscular or intraorgan injection), orally, transdermally, or by vaginal or anal routes, or by other routes of administration, as are well known in the art. Antagonists may be in solid or liquid form and would generally include pharmaceutically acceptable or veterinarially acceptable excipients and/or carriers. Examples of dosage forms which may be used in this invention are those well known in the art as mentioned previously such as described in Remington's Pharmaceutical Sciences (Mack Publishing Company, 10th Edition, which is incorporated herein by reference).

In still another aspect of this invention, there is provided nucleotide sequences encoding $\alpha(1,3)$ galactosyl transferase and mutants thereof. Preferably, the nucleotide sequence encodes pig $\alpha(1,3)$ galactosyl transferase.

Nucleotide sequences may be in the form of DNA, RNA or mixtures thereof. Nucleotide sequences or isolated nucleic acids may be inserted into replicating DNA, RNA or DNA/RNA vectors as are well known in the art, such as plasmids, viral vectors, and the like (Sambrook et al, Molecular Cloning A Laboratory Manual, Cold Spring Harbor Laboratory Press, NY, Second Edition 1989).

Nucleotide sequences encoding $\alpha(1,3)$ galactosyl transferase may include promoters, enhancers and other regulatory sequences necessary for expression, transcription and translation. Vectors encoding such sequences may include restriction enzyme sites for the insertion of additional genes and/or selection markers, as well as elements necessary for propagation and maintenance of vectors within cells.

Mutants of nucleotide sequences encoding $\alpha(1,3)$ galactosyl transferase are particularly preferred as they may be used in homologous recombination techniques as are well known in the art (Capecchi M R, Altering the Genome by Homologous Recombination, Science 244:1288–1292, 1989; Merlino G T, Transgenic Animals in Biomedical research, FASEB J 5:2996–3001, 1991; Cosgrove et al, Mice Lacking MHC Class II Molecules, Cell 66:1051–1066, 1991; Zijlstra et al, Germ-line Transmission of a disrupted B2-microglobulin gene produced by homologous recombination in embryonic stem cells, Nature 342:435, 1989) for the inactivation of wild type $\alpha(1,3)$ galactosyl transferase genes.

Mutant $\alpha(1,3)$ galactosyl transferase nucleotide sequences include nucleotide deletions, insertions, substitutions and additions to wild type $\alpha(1,3)$ galactosyl transferase such that the resultant mutant does not encode a functional galactosyl transferase. These nucleotide sequences may be utilized in homologous recombination techniques. In such techniques, mutant sequences are recombined with wild type genomic sequences in stem cells, ova or newly fertilized cells comprising from 1 to about 500 cells. Nucleotide sequences utilized in homologous recombination may be in the form of isolated nucleic acids sequences or in the context of vectors. Recombination is a random event and on recombination, destruction of the functional gene takes place.

Transgenic animals produced by homologous recombination and other such techniques to destroy wild type gene function are included within this invention, as are organs derived therefrom. By way of example, transgenic pigs may be produced utilizing homologous recombination techniques to produce a transgenic animal having non-functional $\alpha(1-3)$ galactosyl transferase genomic sequences. Tissues derived from such transgenic animals may then be utilized in xenotransplantation into human patients with the avoidance of immune reaction between circulating human antibodies reactive with $Gal\alpha(1-3)Gal$ epitopes. Such transplants are contemplated to be well tolerated by transplant recipients. Whilst transplanted tissue may comprise other antigens which provoke immune reaction beyond those associated with $Gal\alpha(1-3)Gal$ epitopes, removing the major source of the immune reaction with such transplanted tissues should lead to xenotransplants being relatively well tolerated in conjunction with standard rejection therapy (treatment with immune suppressants such as cyclosporin).

This invention will now be described with reference to the following non-limiting Figures and Examples.

BRIEF DESCRIPTION OF THE DRAWINGS

FIG. 1A shows titer of pooled human serum before and after absorption. Titer obtained by hemagglutination on RBC (hatched bars) and resetting assay on PBL (open bars) and spleen cells (solid bars). Absorption studies demonstrated that the same xeno antigens were present on all of these tissues (FIG. 1 and FIG. 2), as absorption with RBC, spleen cells or PBL, removed reactivity for the other cells (FIG. 1A and FIG. 2). Absorption of the serum pool with EC, while removing all of the EC reactive antibodies (FIG. 2A), completely removed all PBL reactive antibodies and almost all the RBC hemagglutinating antibodies (titer fell from $\frac{1}{128}$ to $\frac{1}{2}$) (FIG. 1A). Absorption with RBC removed 75% (FIG. 2B) and spleen cells all (FIG. 2C) of the EC reactive antibodies shown by flow cytometry. Thus, common epitopes are present on pig red cells, PBL, spleen and endothelial cells. Serum absorbed with EC was not tested on PBL or spleen cells. FIG. 1B—see

FIG. 3: Hemagglutination titer of treated and untreated human serum. Untreated human serum (A); protein-A non binding immunoglobulin (B); protein-A eluted immunoglobulin (C); serum treated with 2-mercaptoethanol (D). FIG. 1B shows the same data with the addition of data obtained using a high molecular weight immunoglobulin fraction. FIG. 1B: Untreated human serum (A); protein-A non binding immunoglobulin (B); high molecular weight fraction (C); protein-A eluted immunoglobulin (D); serum treated with 2-mercaptoethanol (E).

Figure 4:
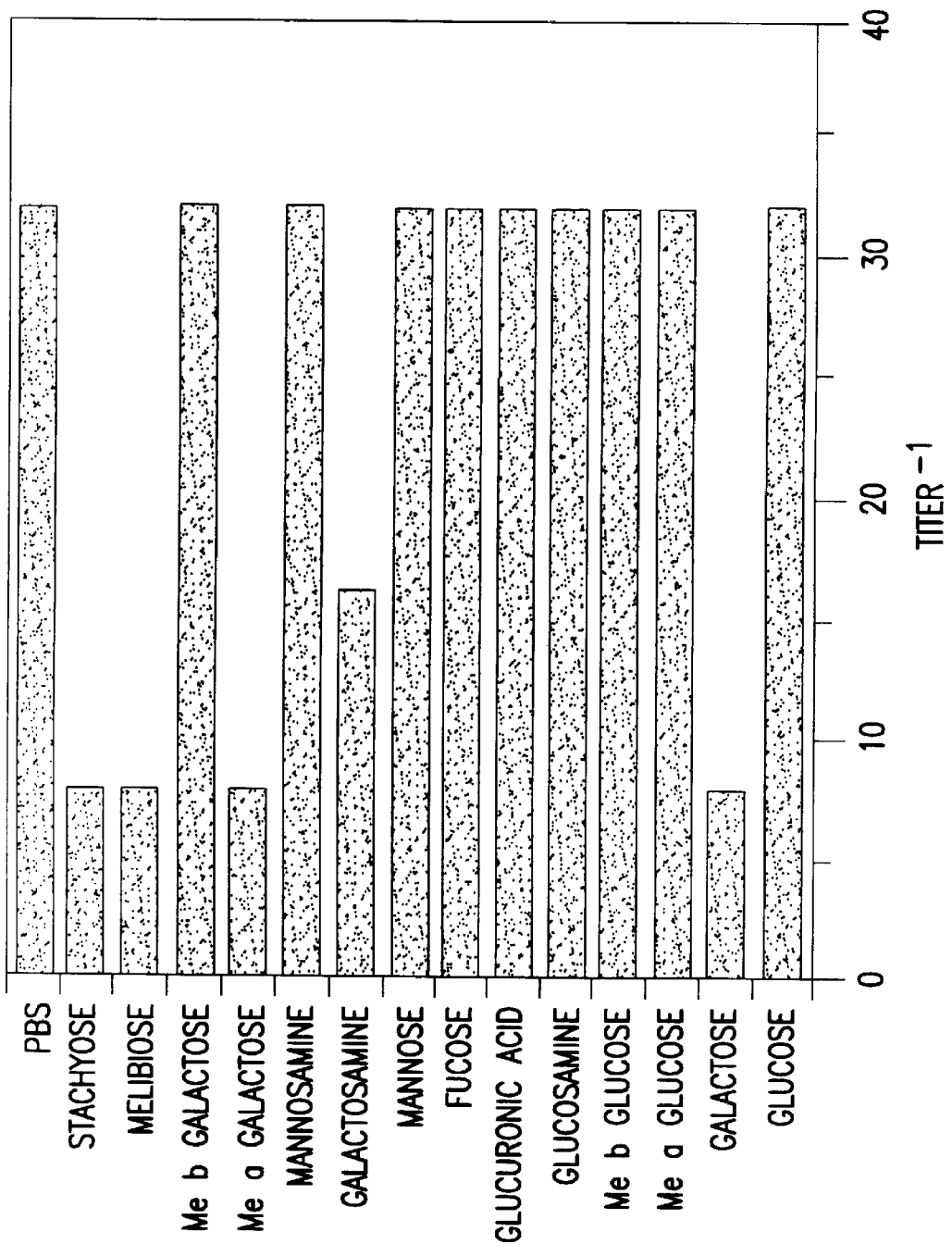
FIG. 4: Carbohydrate inhibition of hemagglutination of normal human serum. Human serum was titered in the presence of 300mM solutions of carbohydrates.

Only carbohydrates inhibiting hemagglutination in FIG. 4 were used in this experiment, with glucose and methyl-β-galactopyranoside as negative controls.

Figure 6:
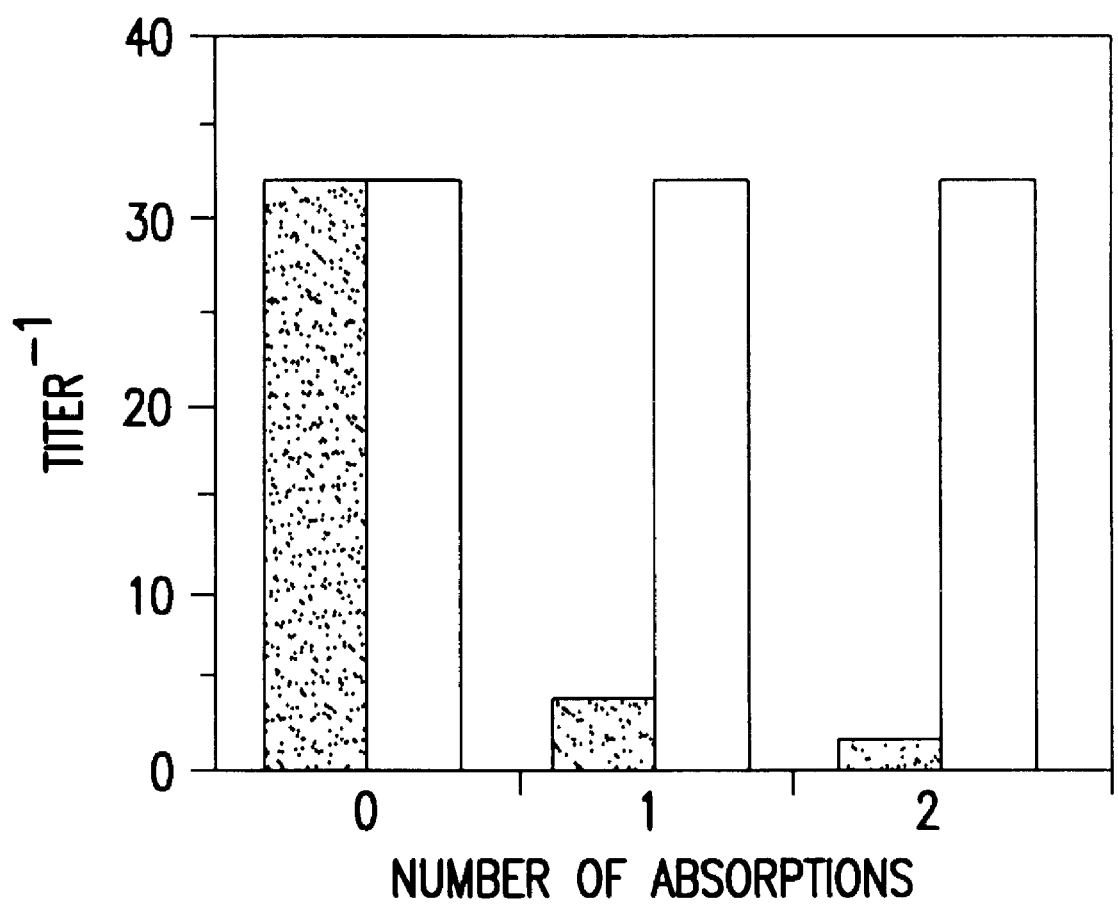

FIG. 6: Hemagglutination titer of human serum on pig RBC pre and post absorption on a melibiose column. Human serum was absorbed with equal volumes of melibiose-sepharose (solid bars) or sepharose (open bars), a number of times as indicated in the figure axis.

Figure 7:
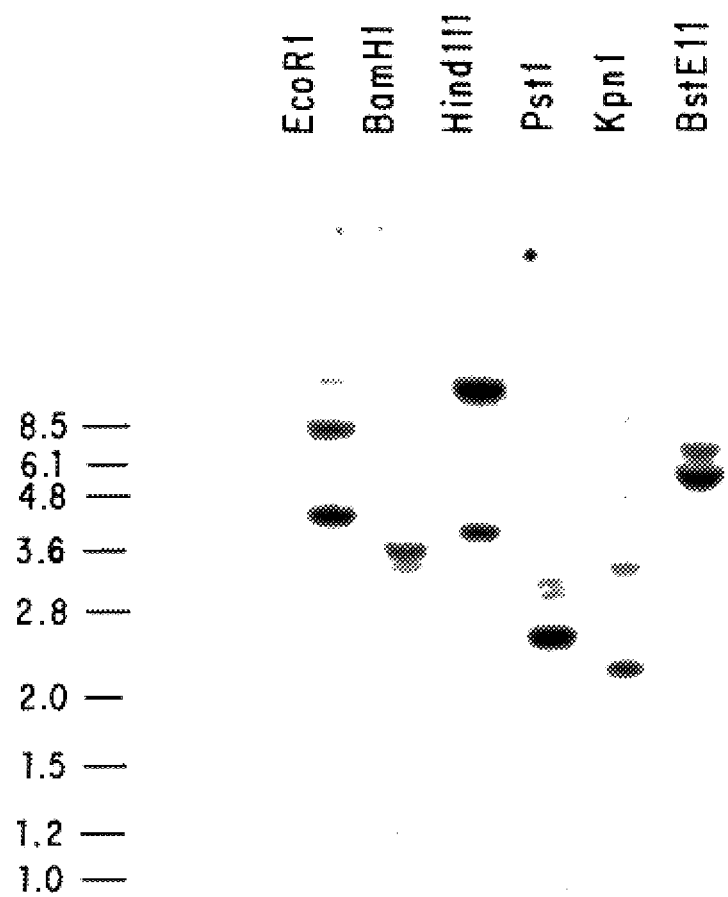

FIG. 7: Southern blot of pig genomic DNA probed with the cDNA insert of clone pPGT-4.

BRIEF DESCRIPTION OF THE SEQUENCE LISTINGS

SEQ ID NO:1 Partial nucleotide and predicted amino acid sequence of the pig Galα(1,3) transferase.

SEQ ID NO:2 Complete nucleotide and predicted amino acid sequence of the pig Galα(1,3) transferase.

SEQ ID NO:3 Nucleotide sequence for PCR primer αGT-1.

SEQ ID NO:4 Nucleotide sequence for PCR primer αGT-2.

With regard to SEQ ID NOS:1–2, it should be noted that the present invention is not limited to the specific sequences shown, but, in addition to the mutations discussed above, also includes changes that are found as naturally occurring allelic variants of the porcine Galα(1,3) galactosyl transferase gene, as well as nucleic acid mutations which do not change the amino acid sequences set forth in these sequences, e.g., third nucleotide changes in degenerate codons.

EXAMPLE 1

Materials and Methods

Cells. Pig cells and tissues were obtained from an abattoir from freshly slaughtered animals. Whole blood was centrifuged at 800 g, and erythrocytes (RBC) obtained and were washed three times in phosphate buffered saline (PBS); pig peripheral blood lymphocytes (PBL) were isolated by density gradient centrifugation using ISOPAQUE FICOLL (Vaughan et al, (1983) Transplantation 36:446–450). Pig splenocytes were obtained from whole spleen by teasing tissue through a sieve to give a single cell suspension. Endothelial cell (EC) cultures were established after treatment of sterile pig aorta with Collagenase Type 4 (Worthington Biochemical Corporation, New Jersey) and the isolated cells were grown in Dulbecco's modified Eagles medium (DMEM) (ICN Biomedicals Australasia Pty Ltd., Seven Hills, NSW) on gelatin coated plates at 37° C. The endothelial origin of EC cultures was verified using rabbit anti human von Willebrand factor antibody (Dako A/S, Copenhagen) and indirect immunofluorescence. COS cells used were maintained in fully supplemented DMEM medium.

Antibodies. Human serum was obtained from a panel of normal volunteers, heat inactivated and pooled before use. The mAb HuLy-m3 (CD48), was used as a negative control (Vaughan Supra). Equal volumes of human serum and 5 to 200 mM 2-mercaptoethanol were incubated at 37° C. for one hour to destroy IgM.

Absorptions. Pooled serum was absorbed with equal volumes of washed, packed cells for 15 minutes at 37° C., for 15 minutes at 4° C., serum obtained and the procedure repeated three times. For the absorption with melibiose-agarose (Sigma, St Louis, Mo.) and sepharose (Pharmacia LKB Biotechnology, Uppsala, Sweden), equal volumes packed beads and serum were incubated at 37° C. for 16 hours, the beads removed by centrifugation, and the absorption repeated several times.

Serological Assays. a) Hemagglutination: 50 μl of 0.1% pig RBC were added to 50 μl of human serum in 96 well plates, incubated at 37° C. for 30 minutes, room temperature for 30 minutes and on ice for 60 minutes prior to both macroscopic and microscopic evaluation of hemagglutination; b) Rosetting: Sheep anti human IgG was coupled to sheep RBC with chromic chloride and used in a rosetting assay (Parish et al (1978) J Immunol. Methods 20:173–183); c) Cytofluorographic analysis was performed on FACScan (Becton Dickinson, San Jose, Calif.) (Vaughan et al (1991) Immunogenetics 33:113–117); d) Indirect immunofluorescence was performed on cell monolayers in 6 well tissue culture plates using fluoresceinated sheep anti human IgM or IgG (Silenus Laboratories Pty Ltd, Hawthorn, Victoria, Australia) (Vaughan Supra).

Sugar Inhibitions. Two types of sugar inhibition assays were performed: a) 50 μl of sugars (300 mM in PBS) were added to 50 μl of doubling dilutions of human serum in 96 well plates, incubated overnight at 46° C. and then 50 μl of 0.1% pig RBC added and the hemagglutination assay performed; b) Human serum, diluted in PBS at one dilution less than that of the 50% hemagglutination titer, was added to 50 μl of doubling dilutions of sugars (starting at 300 mM) and incubated overnight at 4° C., after which 50 μl of 0.1% pig RBC was added and the hemagglutination assay performed.

Murine Gal α(1–3) Transferase cDNA construct. A cDNA clone, encoding the mouse α(1,3)galactosyl transferase was produced using the published sequence of this transferase (Larsen et al (1989) J Biol. Chem 264:14290–14297) and the polymerase chain reaction (PCR) technique. Briefly two oligonucleotides were synthesized; αGT-1 (5'-GAATTCAAGC TTATGATCAC TATGCTTCAA G-3') SEQ ID NO:3 which is the sense oligonucleotide encoding the first six amino acids of the mature αGT and contains a HindIII restriction site, and αGT-2 (5'-GAATTCCTGC AGTCAGACAT TATTCTAAC-3')SEQ ID NO:4 which is the anti-sense oligonucleotide encoding the last 5 amino acids of the mature α(GT and the in phase termination codon and contains a PstI restriction site. This oligonucleotide pair was used to amplify a 1185 bp fragment from a C57BL/6 spleen cell CDNA library (Sandrin et al (1992) J Immunol. 194:1636–1641). The 1185 bp fragment was purified from a Low Gelling point agarose gel, digested with HindIII and PstI (Pharmacia) restriction endonucleases, and directionally cloned into HindIII/PstI digested CDM8 vector (Seed B (1987) Nature 329:840 842) using T4 ligase (Pharmacia). The product of the ligation was used to transform MC1061/p3, and DNA prepared from resultant colonies for further examination. One plasmid (pαGT-3) having the 1185 bp fragment was selected for further studies. Plasmid DNA was prepared, sequenced to confirm the correct DNA sequence, and used for COS cells transfection experiments using DEAE/Dextran (Vaughan et al (1991) Immunogenetics 33: 113–117; Sandrin et al (1992) J Immunol. 194:1636–1641, Seed B (1987) Nature 329:840–842).

EXAMPLE 2

Human Anti-pig Antibodies Detect Epitopes Present on Different Cells

Figure 1A:
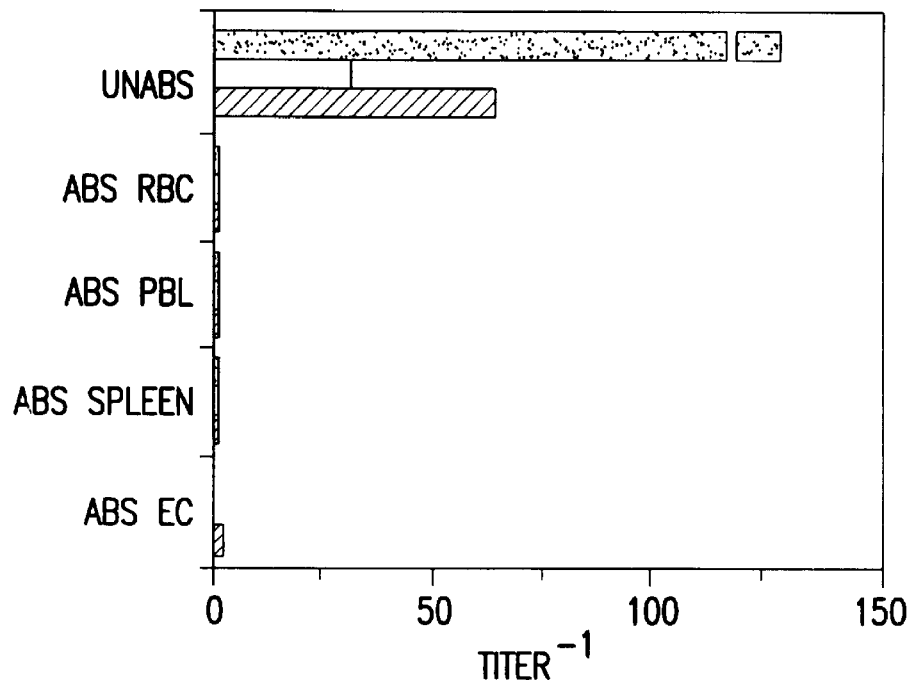
FIGS. 1a–1b.
Figure 1B:
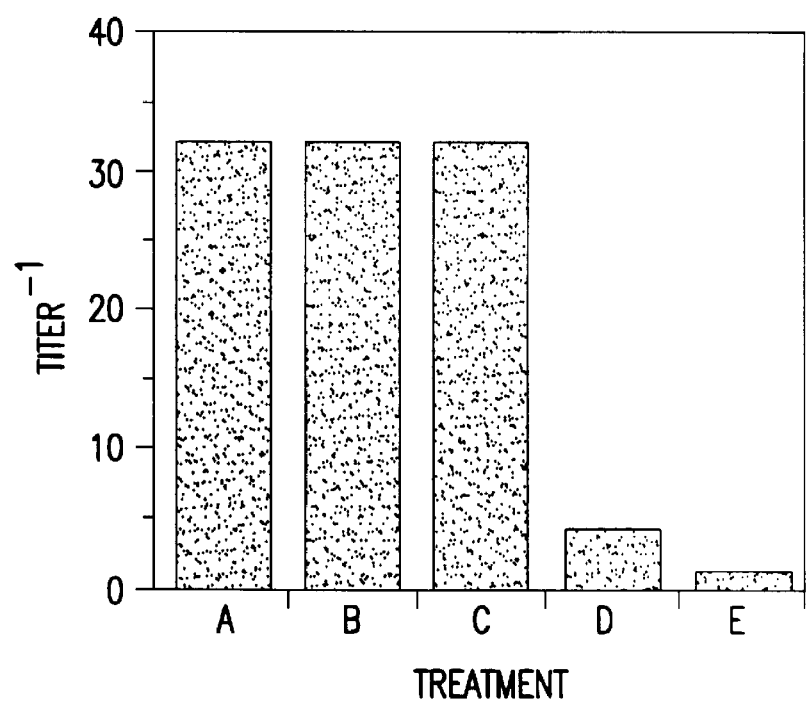
Figure 2A:
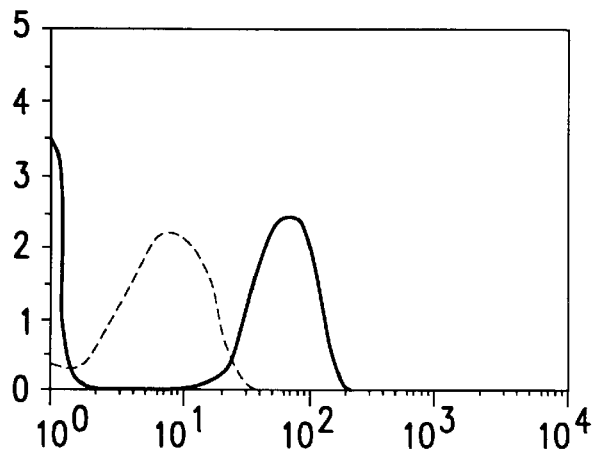
FIGS. 2a–2c: Testing of pig EC with pooled human serum before and after absorption. In each panel EC tested with absorbed serum (dotted line) or non absorbed serum (solid line). Serum absorbed with EC (panel A), RBC (panel B) or spleen cells (panel C). Binding of human antibody was detected using sheep anti-human IgM and analysis by flow cytometry.
Figure 2B:
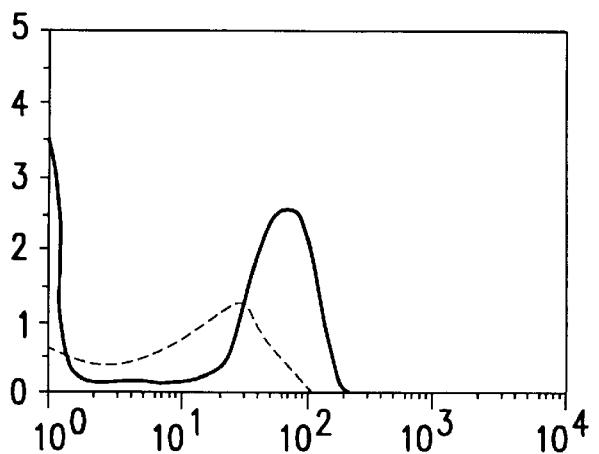
Figure 2C:
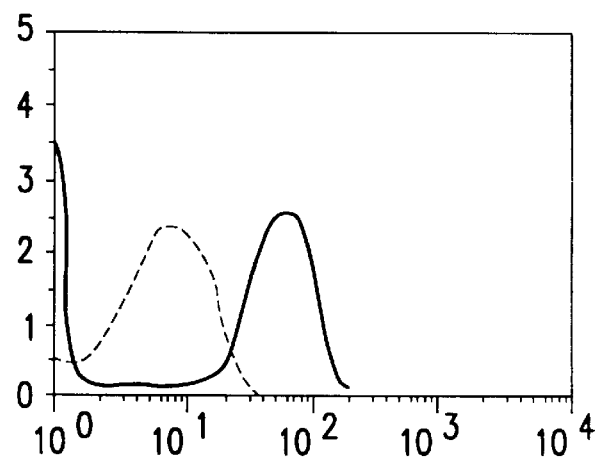

To establish that human serum contains antibodies to pig cells which are predominantly of the IgM class, a pool of human serum was made (from 10 donors) and found to contain antibodies which reacted with pig red cells (by hemagglutination); pig lymphocytes (resetting assay and flow cytometry); pig spleen cells (resetting); and pig endothelial cells (flow cytometry) (FIGS. 1 and 2). Absorption studies demonstrated that the same xeno antigens were present on all of these tissues (FIG. 1 and FIG. 2), as absorption with RBC, spleen cells or PBL, removed reactivity for the other cells (FIG. 1A and FIG. 2). Absorption of the serum pool with EC, while removing all of the EC reactive antibodies (FIG. 2a), completely removed all PBL reactive antibodies and almost all the RBC hemagglutinating antibodies (titer fell from 1/128 to 1/2) (FIG. 1A). Absorption with RBC removed 75% (FIG. 2B) and spleen cells all (FIG. 2C) of the EC reactive antibodies shown by flow cytometry. Thus, common epitopes are present on pig red cells, PBL, spleen and endothelial cells.

Figure 3:
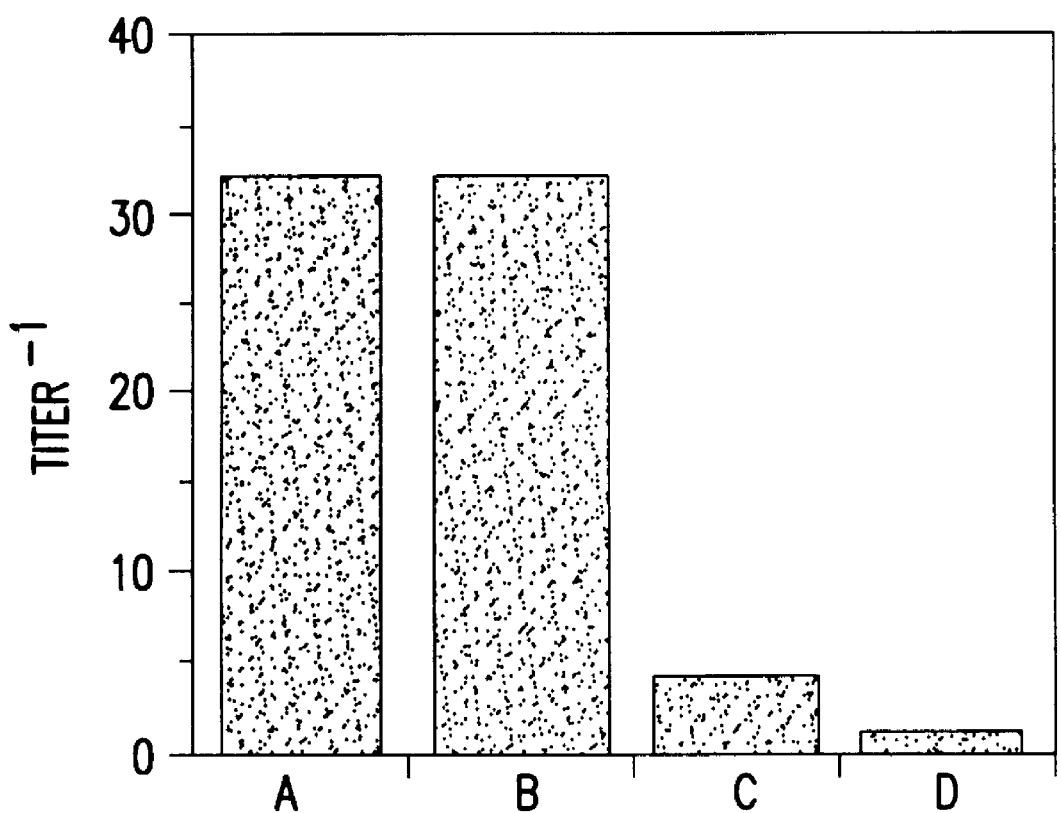
FIG. 3.

Most of the activity in the serum pool was due to IgM rather than IgG antibodies as indicated by the inability of a protein A-sepharose column, which does not bind IgM, to alter the titer of the serum after passage through the column (FIG. 3), and IgG antibodies eluted from the protein A-sepharose column reacted only weakly with RBC (FIG. 3). Furthermore, treatment of the serum with 2-mercaptoethanol, which destroys IgM but leaves IgG intact, led to a complete loss of antibody activity (FIG. 3). When the serum was fractionated by SEPHACRYL gel chromatography, the high molecular weight fractions (IgM) were reactive with RBC, whereas the low molecular weight fractions (IgG) were not (data not shown). Thus the different pig cells carry similar epitopes, all reacted with IgM antibodies and in our assays there was little IgG activity found in the human serum for pig cells.

EXAMPLE 3

Human Anti-pig Antibodies React Predominantly With Terminal Galactose Residues

The ability of different carbohydrates to inhibit the hemagglutination reaction (FIG. 4) was examined. Of the sugars tested, inhibition as measured by a decrease in titer, was observed with 300 mM galactose, methyl-α-D-galactopyranoside, melibiose and stachyose, all of which decreased the titer of the serum pool by 750 (FIG. 4); and with 300 mM D-galactosamine, for which a 50% decrease in titer was observed (FIG. 4). None of the other monosaccharides tested (listed in the figure legend) had any effect on hemagglutination titer (FIG. 4). These studies demonstrated that galactose is the part of the epitope, as both melibiose and stachyose have terminal galactose residues. It is of interest to note the difference in the ability of galactose in the α(methyl-α-D-galactopyranoside, melibiose and stachyose) but not β(methyl-βD-galactopyranoside) configuration to inhibit the serum.

Figure 5:
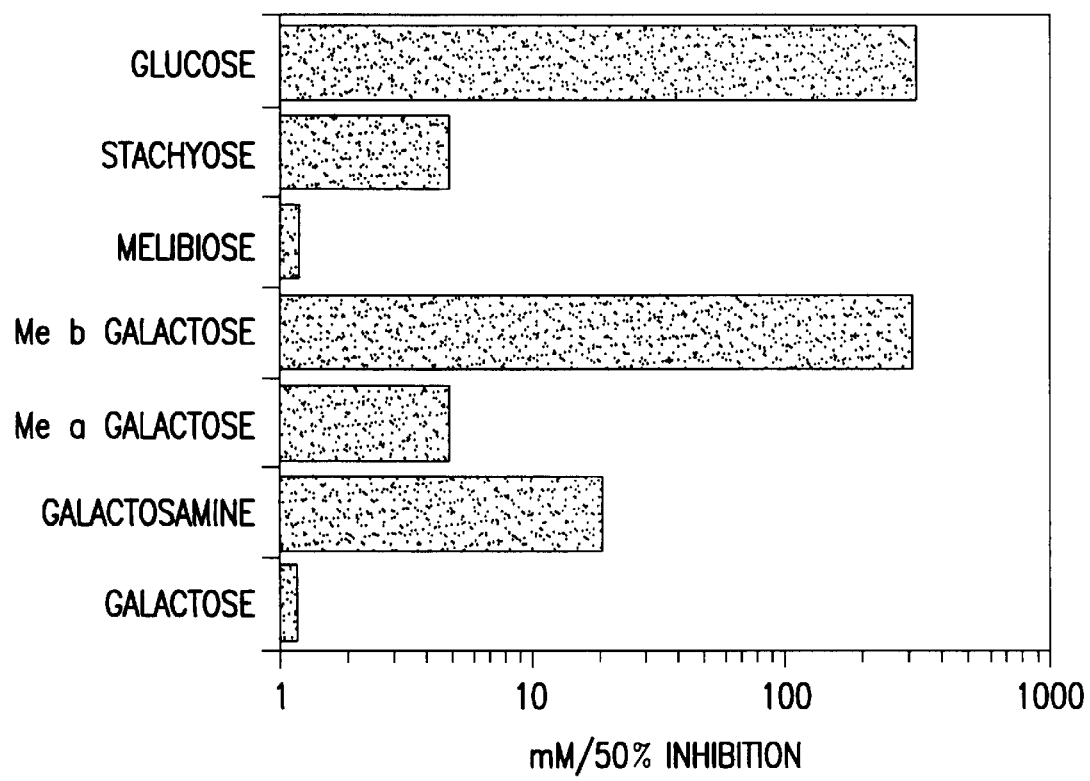
FIG. 5: Concentration of carbohydrate giving 50% inhibition of hemagglutination titer of normal human serum.

The relative avidity of the antibodies for the sugars which inhibited agglutination was estimated from the concentration of sugar giving 50% inhibition of the agglutination titer (FIG. 5). Both D-galactose and melibiose achieved this inhibition at <1.5 mM, stachyose and methyl-α-D-galactopyranoside at 4.7 mM and D-galactosamine at 18.7 mM (FIG. 5). By contrast, D-glucose and methyl-β-D-galactopyranoside had no effect even at 300 mM concentration. Thus D-galactose is an important part of the epitope, as it is a potent inhibitor of the xenoantibodies at low concentration (<1.15 mM); the ability of methyl-α-D-galactopyranoside to inhibit agglutination at low concentrations (<1.15 mM), compared with the failure of methyl-β-D-galactopyranoside (300 mM) to inhibit, demonstrates that the galactose residue (which is likely to be a terminal sugar) is in an α-linkage rather than a β-linkage with the subterminal residue. The results obtained with melibiose (Galα(1,6)Glc) and stachyose (Galα(1,6)Galα(1,6)Glcβ(1,2)Fru), which have α-linked terminal galactose residues, are in accord with this conclusion. The inhibition of hemagglutination observed with galactosamine, which has an additional amine side chain on galactose, (50% inhibition of titer at 18.7 mM) could be due to a second carbohydrate involved in the epitope, or a lower affinity of the xenoantibodies for this sugar.

To further examine the reaction with galactose, the serum pool was absorbed four times with equal volumes of packed melibiose sepharose or with sepharose as the control (FIG. 6), one absorption with melibiose-sepharose decreased the titer of the antibody from 1/32 to 1/4, and two sequential absorptions decreased the titer further to 1/2 (FIG. 6). This absorption was specific for melibiose, as using sepharose beads had no effect (FIG. 6). Thus the majority of the antibody (=94%) reactive with xenoantigens reacts with galactose in an β-linkage.

EXAMPLE 4

Human Anti-Pig Antibodies React with COS Cells After Transfection with α(1,3) Galactosyl Transferase The cDNA coding for the α(1,3)galactosyl transferase which transfers a terminal galactose residue with an α(1,3) linkage to a subterminal galactose has been cloned for both mouse (Larsen et al (1989) J Biol Chem 264:14290–14297) and ox (Joziasse et al (1989) J Biol Chem 264:14290–14297). Using this data we used transfection experiments to determine the role of the Galα(1,3)Gal epitope in isolation of others. The mouse transferase was isolated from a cDNA library using the PCR technique, and the PCR product was directionally cloned into the CDM8 vector for expression studies in COS cells. The cDNA insert was sequenced in both directions and shown to be identical to the published nucleotide sequence (Larsen et al (1989) J Biol Chem 264:14290–14297). COS cells, derived from Old World Monkeys, were chosen as they do not react with human serum nor with the IB-4 lectin (which is specific for the Galα(1,3)Gal epitope) (Table 1). After transfection of COS cells with the α(1,3)galactosyl transferase, the Galα(1,3)Gal epitope was detected on the cell surface by binding of the IB-4 lectin (Table 1); these cells were also strongly reactive with the serum pool. Absorbing the human sera with pig RBC removed the reactivity for Galα(1,3)Gal$^+$COS cells, (Table 1). Passage of the serum over a protein-A sepharose column had no effect on the reactivity of the serum for Galα(1,3)Gal$^+$COS cells, when using an FITC conjugated sheep anti-human IgM as the second antibody (this was reflected in the same number of reactive cells, the intensity of staining and the titer of the serum (Table 1)). In contrast to this, eluted antibodies reacted only weakly with the Galα(1,3)Gal$^+$COS cells, and this reaction was only observed when using FITC conjugated sheep anti-human IgG or FITC conjugated sheep anti-human Ig, but not FITC conjugated sheep anti human IgM (Table 1). Thus human serum has IgM antibodies to the Galα(1,3)Gal epitope which was expressed on Galα(1,3)Gal$^+$COS cells. The reaction of the serum with Galα(1,3)Gal$^+$COS cells is specific and not due to the transfection procedure as CD48$^+$COS cells were not reactive with either the serum nor the IB-4 lectin (Table 1). Furthermore, the reactivity for both pig RBC (as detected by hemagglutination) and EC (as detected by FACS analysis) could be removed by absorption with Galα(1,3)Gal⁺COS cells but not untransfected COS cells. Thus human serum pool contains IgM antibodies reactive with the Galα(1,3)Gal epitope.

The level of antibodies in human serum reactive with the Galα(1,3)Gal epitope can be used to determine the propensity of a patient to hyperacutely reject a porcine xenotransplant. In addition, the level of such antibodies can be used to determine the amount of antibody antagonist that should be administered to a patient prior to such xenotransplantation.

The level of these antibodies can be effectively determined using the transfected and untransfected COS cells described above as matched Galα(1,3)Gal⁺ and Galα(1,3)Gal⁻ absorbants, followed by a measurement of the reactivity of the absorbed serum for pig RBC and/or EC. Higher levels of serum antibody will result in a larger difference in reactivity of the serum absorbed against the Galα(1,3)Gal⁺ absorbant versus that absorbed against the Galα(1,3)Gal⁻ absorbant. Cells from other species, e.g., human cells, can be used in such an assay. Also, rather than using a DNA sequence encoding the murine transferase, a DNA sequence encoding the porcine transferase (see Example 5) can be used. Such a porcine transferase is preferred since there may be differences in the action of the murine and porcine transferases, e.g., altered sensitivity to the macromolecular environment of the galactose substrate of the enzyme, and for a porcine xenotransplantation, it is the level of antibodies against the Galα(1,3)Gal epitope in the porcine macromolecular environment that is of interest.

In addition to the foregoing, the transfected Galα(1,3)Gal⁺ cells described above can also be used as absorbants to remove anti-Galα(1,3)Gal antibodies from human serum, e.g., by binding such cells to a solid support and passing the serum over the immobilized cells.

EXAMPLE 5
Cloning of Porcine α(1,3) Galactosyl Transferase

Utilizing the murine cDNA clone for the α(13) galactosyl transferase as a hybridization probe we have cloned the pig α(1,3) galactosyl transferase from a λGT11 pig spleen cDNA library (Clontech Laboratories, Palo Alto, Calif.) according to standard methods as described in Sambrook et al (supra). This clone, pPGT-4, has been deposited with the AGAL and assigned accession number N94/9030. SEQ ID NO:1 shows a partial nucleotide sequence and predicted amino acid sequence of pig Galα(1,3) transferase as determined by sequencing of clone pPGT-4. The sequence shown is incomplete at the 5' end.

Utilizing the cDNA insert of the pPGT-4 clone as a hybridization probe we have also cloned the 5' end of the pig α(1,3) galactosyl transferase from a 5' STRECH pig liver cDNA library in λgt10, according to standard methods as described in Sambrook et al (supra). The insert was obtained by the PCR technique using a λ oligonucleotide, and an oligonucleotide made to the pig sequence. This PCR product was subcloned into SmaI cut pBLUESCRIPT KS⁺. This clone, pPGT-2, has been deposited with the AGAL and assigned accession number N94/9029.

SEQ ID NO:2 shows a complete nucleotide sequence and predicted amino acid sequence of pig Galα(1,3) transferase as determined by sequencing of clones pPGT-4 and pPGT-2. The pig transferase has high sequence homology with both the murine and bovine α(1,3) galactosyl transferase genes.

Both the partial and complete cDNA sequences of SEQ ID NOS:1–2 can be used in the xenotransplant therapies discussed above. For example, using techniques well known in the art, all or a part of any of the nucleotide sequences of SEQ ID NOS:1–2, when inserted into replicating DNA, RNA or DNA/RNA vectors, can be used to reduce the expression of the Galα(1,3) transferase in porcine cells by directing the expression of anti-sense RNAs in transgenic cells or animals. See, for example, Biotechniques, 6(10):958–976, 1988.

In addition, as illustrated in the following example, the sequences of SEQ ID NOS:1–2 can be used as hybridization probes for the characterization and isolation of genomic clones encoding the porcine Galα(1,3) transferase. Mutants of the genomic nucleotide sequence, in turn, can be used in homologous recombination techniques of the types described above so that destruction of the functional gene takes place in porcine cells.

EXAMPLE 6

Characterization and Isolation of the Porcine Gene Encoding α(1,3) Galactosyl Transferase Genomic DNA prepared from pig spleen tissue was digested with EcoR1, BamH1, Pst1, HindIII, Kon1 and BstEII, electrophoresed on a 0.8% agarose gel and transferred to a nylon filter, the final wash was at 65° C. in 0.1×SSC, 0.1% SDS. As shown in FIG. 7, the genomic Southern blot demonstrated a simple pattern suggesting that the gene exists as a single copy with a genomic size of ≈25kb.

Utilizing the cDNA insert of the pPGT-4 clone as a hybridization probe, we have cloned the porcine α(1,3) galactosyl transferase gene from a pig genomic DNA EMBL library (Clontech Laboratories, Inc., Palo Alto, Calif.) according to standard methods as described in Sambrook et al (supra). This cloning has resulted in the isolation of two lambda phage clones, λPGT-g1 and λPGT-g5 that contain different regions of the porcine transferase gene.

As discussed above, the gene for the α(1,3) galactosyl transferase can be used to effect targeted destruction of the native gene for this enzyme using homologous recombination technology. In accordance with the conventional techniques used in this art, such gene knockout is performed using fragments obtained from genomic clones of the type provided by this example. The gene destruction can be performed in somatic or stem cells (Capecchi, 1989, supra). Because such genetically engineered cells do not produce the Galα(1,3)Gal epitope, they and their progeny are less likely to induce hyperacute rejection in humans and are thus suitable for xenotransplantation into human patients.

EXAMPLE 7

Production of Anti-idiotypic Antibodies Against Human Anti-Galα(1,3)Gal Antibodies Polyclonal anti-idiotypic antibodies against human anti-Galα(1,3)Gal antibodies are prepared following the procedures of Coligan, et al., 1992, supra; Harlow and Lane, 1988, supra; and Liddell and Cryer, 1991, supra. Human anti-Galα(1,3)Gal antibodies are absorbed from pooled human serum onto immobilized melibiose (melibiose-sepharose or melibiose-agarose) as described above in Example 3. The antibodies are eluted using standard methods, such as, high or low pH, high salt, and/or chaotropic agents. Fab' fragments are prepared following dialysis into an appropriate buffer. The Fab' fragments are used to immunize rabbits, goats, or other suitable animals, along with conventional adjuvants.

The resulting polyclonal antisera are tested for their ability to change the conformation of the human antibody reactive site so as to reduce its affinity for the Galα(1,3)Gal epitope. Those sera that produce such reduced affinity constitute the desired anti-idiotypic antibodies.

Monoclonal antibodies are produced using the same Fab' fragments as antigens to immunize appropriate strains of mice. Hybridomas are prepared by fusing spleen cells from such immunized mice with murine myeloma cells. Supernatants are tested for antibodies having the ability to change the conformation of the human antibody reactive site so as to reduce its affinity for the Galα(1,3)Gal epitope. Those antibodies that produce such reduced affinity constitute the desired monoclonal anti-idiotypic antibodies.

The finding that the majority of xenoreactive IgM is directed to the enzymatic product of the single transferase raises the possibility of producing transgenic pigs lacking the epitope, by targeted destruction of the α(1,3) galactosyl transferase genes using homologous recombination technology. Such genetically modified pigs could be used for transplantation. The destruction of the gene is likely to have no deleterious effect on the pig—humans live normally in its absence.

This invention has been described by way of example only and is in no way limited by the specific examples herewith.

DEPOSITS

Clones pPGT-4, pPGT-2, λPGT-g1, and λPGT-g5, discussed above, have been deposited with the Australian Government Analytical Laboratories, (AGAL), 1 Suakin Street, Pymble, N.S.W. 2073, Australia, and have been assigned the designations N94/9030, N94/9029, N94/9027, and N94/9028, respectively. These deposits were made under the Budapest Treaty on the International Recognition of the Deposit of Micro-organisms for the Purposes of Patent Procedure (1977). These deposits were made on Mar. 11, 1994.

TABLE 1

Serology On Transfected COS Cells

| Serum | Target | Reaction[1] |
|---|---|---|
| NHS | $GT^+COS$ | +++ |
| NHS abs RBC | $GT^+COS$ | − |
| NHS Tx 2-ME | $GT^+COS$ | − |
| NHS abs Protein A | $GT^+COS$ | +++[2] |
| NHS Eluted Protein A | $GT^+COS$ | +[3] |
| CD48 | $GT^+COS$ | − |
| NHS | $CD48^+COS$ | − |
| CD48 | $CD48^+COS$ | +++ |
| NHS | COS | − |
| CD48 | COS | − |
| IB4[4] | $GT^+COS$ | +++ |
| IB4 | $CD48^+COS$ | − |
| IB4 | COS | − |

[1]Reactivity detected by indirect immunofluorescence using FITC conjugated sheep anti-human Ig or FITC conjugated sheep anti-mouse Ig unless otherwise stated.
[2]No difference in titer was observed when tested with FITC conjugated sheep anti-human IgM.
[3]Reaction detected on protein A purified immunoglobulin using FITC conjugated sheep anti-human Ig or FITC conjugated sheep anti-human IgG, but not with FITC conjugated sheep anti-human IgM.
[4]Reactivity detected using FITC conjugated IB4 lectin.

What is claimed is:

1. An isolated nucleic acid molecule comprising:
 (a) the nucleic acid sequence of SEQ ID NO:1; or
 (b) an antisense sequence complementary to (a); or
 (c) both (a) and (b).

2. An isolated nucleic acid molecule comprising:
 (a) the nucleic acid sequence of SEQ ID NO:2; or
 (b) an antisense sequence complementary to (a); or
 (c) both (a) and (b).

3. Clone pPgt-4 having deposit designation number AGAL N94/9030.

4. Clone pPGT-2 having deposit designation number AGAL N94/9029.

5. Clone λPGT-g1 having deposit designation number AGAL N94/9027.

6. Clone λPGT-g5 having deposit designation number AGAL N94/9028.

7. A porcine cell comprising an inactivated porcine α (1,3) galactosyl transferase gene, said inactivated porcine α (1,3) galactosyl transferase gene comprising a wild type porcine α (1,3) galactosyl transferase sequence disrupted by a cloned mutant porcine α (1,3) galactosyl transferase sequence, wherein the cloned mutant porcine α (1,3) galactosyl transferase sequence comprises a mutation of SEQ ID NO:1, wherein the mutation is selected from the group consisting of a deletion, an insertion, a substitution, and an addition such that the cloned mutant porcine α (1,3) galactosyl transferase sequence does not encode a functional galactosyl transferase so that immune reaction of the cell with human antibodies reactive with Gal α (1,3) Gal epitooes is avoided.

8. A porcine cell comprising an inactivated porcine α (1,3) galactosyl transferase gene, said inactivated porcine α (1,3) galactosyl transferase gene comprising a wild type porcine α (1,3) galactosyl transferase sequence disrupted by a cloned mutant porcine α (1,3) galactosyl transferase sequence, wherein the cloned mutant porcine α (1,3) galactosyl transferase sequence comprises a mutation of SEQ ID NO:2, wherein the mutation is selected from the group consisting of a deletion, an insertion, a substitution, and an addition such that the cloned mutant porcine α (1,3) galactosyl transferase sequence does not encode a functional galactosyl transferase so that immune reaction of the cell with human antibodies reactive with Gal α (1,3) Gal epitopes is avoided.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1353 base pairs
( B ) TYPE: Nucleic Acid
( C ) STRANDEDNESS: Double
( D ) TOPOLOGY: Linear ( i i ) MOLECULE TYPE: cDNA to mRNA
( A ) DESCRIPTION: galactosyl transferase, 3' clone ( i i i ) HYPOTHETICAL: No ( i v ) ANTI-SENSE: No ( v i ) ORIGINAL SOURCE:
( A ) ORGANISM: Sus scrofa ( x i ) SEQUENCE DESCRIPTION: SEQ ID NO:1:

```
GTA CCG AGC TCG AAT TCC GCA AGC CAG TCA CCA CAA GCC ATG          42
Val Pro Ser Ser Asn Ser Ala Ser Gln Ser Pro Gln Ala Met
            50                  55                  60

ACT GAC CCA TGT TCC CCC AGA CTG TCG TAC CTT AGC AAA GCC          84
Thr Asp Pro Cys Ser Pro Arg Leu Ser Tyr Leu Ser Lys Ala
                65                  70

ATC CTG ACT CTA TGT TTT GTC ACC AGG AAA CCC CCA GAG GTC         126
Ile Leu Thr Leu Cys Phe Val Thr Arg Lys Pro Pro Glu Val
```

-continued

|  |  |  |  |  |  |  |  |  |  |  |  |  |  |
|---|---|---|---|---|---|---|---|---|---|---|---|---|---|
| 75 | | | | | 80 | | | | | 85 | | | |

```
GTG  ACC  ATA  ACC  AGA  TGG  AAG  GCT  CCA  GTG  GTA  TGG  GAA  GGC        168
Val  Thr  Ile  Thr  Arg  Trp  Lys  Ala  Pro  Val  Val  Trp  Glu  Gly
          90                  95                  100

ACT  TAC  AAC  AGA  GCC  GTC  TTA  GAT  AAT  TAT  TAT  GCC  AAA  CAG        210
Thr  Tyr  Asn  Arg  Ala  Val  Leu  Asp  Asn  Tyr  Tyr  Ala  Lys  Gln
               105                    110                   115

AAA  ATT  ACC  GTG  GGC  TTG  ACG  GTT  TTT  GCT  GTC  GGA  AGA  TAC        252
Lys  Ile  Thr  Val  Gly  Leu  Thr  Val  Phe  Ala  Val  Gly  Arg  Tyr
               120                    125                       130

ATT  GAG  CAT  TAC  TTG  GAG  GAG  TTC  TTA  ATA  TCT  GCA  AAT  ACA        294
Ile  Glu  His  Tyr  Leu  Glu  Glu  Phe  Leu  Ile  Ser  Ala  Asn  Thr
                    135                    140

TAC  TTC  ATG  GTT  GGC  CAC  AAA  GTC  ATC  TTT  TAC  ATC  ATG  GTG        336
Tyr  Phe  Met  Val  Gly  His  Lys  Val  Ile  Phe  Tyr  Ile  Met  Val
145                      150                         155

GAC  GAT  ATC  TCC  AGG  ATG  CCT  TTG  ATA  GAG  CTG  GGT  CCT  CTG        378
Asp  Asp  Ile  Ser  Arg  Met  Pro  Leu  Ile  Glu  Leu  Gly  Pro  Leu
          160                    165                        170

CGT  TCC  TTT  AAA  GTG  TTT  GAG  ATC  AAG  TCC  GAG  AAG  AGG  TGG        420
Arg  Ser  Phe  Lys  Val  Phe  Glu  Ile  Lys  Ser  Glu  Lys  Arg  Trp
               175                    180                       185

CAA  GAC  ATC  AGC  ATG  ATG  CGC  ATG  AAG  ACC  ATC  GGG  GAG  CAC        462
Gln  Asp  Ile  Ser  Met  Met  Arg  Met  Lys  Thr  Ile  Gly  Glu  His
                    190                    195                       200

ATC  CTG  GCC  CAC  ATC  CAG  CAC  GAG  GTG  GAC  TTC  CTC  TTC  TGC        504
Ile  Leu  Ala  His  Ile  Gln  His  Glu  Val  Asp  Phe  Leu  Phe  Cys
                         205                    210

ATT  GAC  GTG  GAT  CAG  GTC  TTC  CAA  AAC  AAC  TTT  GGG  GTG  GAG        546
Ile  Asp  Val  Asp  Gln  Val  Phe  Gln  Asn  Asn  Phe  Gly  Val  Glu
215                      220                         225

ACC  CTG  GGC  CAG  TCG  GTC  GCT  CAG  CTA  CAG  GCC  TGG  TGG  TAC        588
Thr  Leu  Gly  Gln  Ser  Val  Ala  Gln  Leu  Gln  Ala  Trp  Trp  Tyr
          230                    325                        240

AAG  GCA  CAT  CCT  GAC  GAG  TTC  ACC  TAC  GAG  CGG  CCG  AAG  GAG        630
Lys  Ala  His  Pro  Asp  Glu  Phe  Thr  Tyr  Glu  Arg  Pro  Lys  Glu
               245                    250                       255

TCC  GCA  GCC  TAC  ATT  CCG  TTT  CGC  CAG  GGG  GAT  TTT  TAT  TAC        672
Ser  Ala  Ala  Tyr  Ile  Pro  Phe  Arg  Gln  Gly  Asp  Phe  Tyr  Tyr
                    260                    265                       270

CAC  GCA  GCC  ATT  TTG  GGG  GGA  ACA  CCC  ACT  CAG  GTT  CTA  AAC        714
His  Ala  Ala  Ile  Leu  Gly  Gly  Thr  Pro  Thr  Gln  Val  Leu  Asn
                         275                    280

ATC  ACT  CAG  GAG  TGC  TTC  AAG  GGA  ATC  CTC  CAG  GAC  AAG  GAA        756
Ile  Thr  Gln  Glu  Cys  Phe  Lys  Gly  Ile  Leu  Gln  Asp  Lys  Glu
285                      290                         295

AAT  GAC  ATA  GAA  GCC  GAG  TGG  CAT  GAT  GAA  AGC  GGG  CTA  AAC        798
Asn  Asp  Ile  Glu  Ala  Glu  Trp  His  Asp  Glu  Ser  Gly  Leu  Asn
          300                    305                        310

AAG  TAT  TTC  CTT  CTC  AAC  AAA  CCC  ACT  AAA  ATC  TTA  TCC  CCA        840
Lys  Tyr  Phe  Leu  Leu  Asn  Lys  Pro  Thr  Lys  Ile  Leu  Ser  Pro
               315                    320                       325

GAA  TAC  TGC  TGG  GAT  TAT  CAT  ATA  GGC  ATG  TCT  GTG  GAT  ATT        882
Glu  Tyr  Cys  Trp  Asp  Tyr  His  Ile  Gly  Met  Ser  Val  Asp  Ile
                    330                    335                       340

AGG  ATT  GTC  AAG  GGG  GCT  TGG  CAG  AAA  AAA  GAG  TAT  AAT  TTG        924
Arg  Ile  Val  Lys  Gly  Ala  Trp  Gln  Lys  Lys  Glu  Tyr  Asn  Leu
                         345                    350

GTT  AGA  AAT  AAC  ATC  TGACTTTAAA  TTGTGCCAGC  AGTTTTCTGA               969
Val  Arg  Asn  Asn  Ile
```

355

| | | | | | |
|---|---|---|---|---|---|
| ATTTGAAAGA | GTATTACTCT | GGCTACTTCC | TCAGAGAAGT | AGCACTTAAT | 1019 |
| TTTAACTTTT | CAAAAAATAC | TAACAAAATA | CCAACACAGT | AAGTACATAT | 1069 |
| TATTCTTCCT | TGCAACTTTG | AGCCTTGTCA | AATGGGAGAA | TGACTCTGTA | 1119 |
| GTAATCAGAT | GTAAATTCCC | AATGATTTCT | TATCTGCGGA | ATTCCAGCTG | 1169 |
| AGCGCCGGTC | CTACCATTAC | CAGTTGGTCT | GGTGTCGACG | ACTCCTGGAG | 1219 |
| CCCGTCAGTA | TCGGCGGAAT | TCGCGGCCGG | GCGCCAATGC | ATTGGGCCCA | 1269 |
| ATTCCGCCCT | ATAGTGAGTC | GTATTACAAT | TCACTGGCCG | TGTTTTACAA | 1319 |
| CCTCGTGACT | GGGAAAACCC | TGGCCTTACC | CAAC | | 1353 |

( 2 ) INFORMATION FOR SEQ ID NO:2:

( i ) SEQUENCE CHARACTERISTICS:
        ( A ) LENGTH: 1423 base pairs
        ( B ) TYPE: Nucleic Acid
        ( C ) STRANDEDNESS: Double
        ( D ) TOPOLOGY: Linear ( i i ) MOLECULE TYPE: cDNA to mRNA
        ( A ) DESCRIPTION: galactosyl transferase,
                full coding sequence ( i i i ) HYPOTHETICAL: No ( i v ) ANTI-SENSE: No ( v i ) ORIGINAL SOURCE:
        ( A ) ORGANISM: Sus scrofa ( x i ) SEQUENCE DESCRIPTION: SEQ ID NO:2:

| | | | | | |
|---|---|---|---|---|---|
| CGGGGGCCAT | CCCCGAGCGC | ACCCAGCTTC | TGCCGATCAG | GAGAAAATA | 49 |

| | | | | | | | | | | | | | |
|---|---|---|---|---|---|---|---|---|---|---|---|---|---|
| ATG | AAT | GTC | AAA | GGA | AGA | GTG | GTT | CTG | TCA | ATG | CTG | CTT | GTC | 91 |
| Met | Asn | Val | Lys | Gly | Arg | Val | Val | Leu | Ser | Met | Leu | Leu | Val | |
| | | | | 5 | | | | | 10 | | | | | |
| TCA | ACT | GTA | ATG | GTT | GTG | TTT | TGG | GAA | TAC | ATC | AAC | AGA | AAC | 133 |
| Ser | Thr | Val | Met | Val | Val | Phe | Trp | Glu | Tyr | Ile | Asn | Arg | Asn | |
| 15 | | | | 20 | | | | | 25 | | | | | |
| CCA | GAA | GTT | GGC | AGC | AGT | GCT | CAG | AGG | GGC | TGG | TGG | TTT | CCG | 175 |
| Pro | Glu | Val | Gly | Ser | Ser | Ala | Gln | Arg | Gly | Trp | Trp | Phe | Pro | |
| | 30 | | | | 35 | | | | | 40 | | | | |
| AGC | TGG | TTT | AAC | AAT | GGG | ACT | CAC | AGT | TAC | CAC | GAA | GAA | GAA | 217 |
| Ser | Trp | Phe | Asn | Asn | Gly | Thr | His | Ser | Tyr | His | Glu | Glu | Glu | |
| | | 45 | | | | 50 | | | | | 55 | | | |
| GAC | GCT | ATA | GGC | AAC | GAA | AAG | GAA | CAA | AGA | AAA | GAA | GAC | AAC | 259 |
| Asp | Ala | Ile | Gly | Asn | Glu | Lys | Glu | Gln | Arg | Lys | Glu | Asp | Asn | |
| | | | 60 | | | | | 65 | | | | | 70 | |
| AGA | GGA | GAG | CTT | CCG | CTA | GTG | GAC | TGG | TTT | AAT | CCT | GAG | AAA | 301 |
| Arg | Gly | Glu | Leu | Pro | Leu | Val | Asp | Trp | Phe | Asn | Pro | Glu | Lys | |
| | | | | 75 | | | | | 80 | | | | | |
| CGC | CCA | GAG | GTC | GTG | ACC | ATA | ACC | AGA | TGG | AAG | GCT | CCA | GTG | 343 |
| Arg | Pro | Glu | Val | Val | Thr | Ile | Thr | Arg | Trp | Lys | Ala | Pro | Val | |
| 85 | | | | | 90 | | | | | 95 | | | | |
| GTA | TGG | GAA | GGC | ACT | TAC | AAC | AGA | GCC | GTC | TTA | GAT | AAT | TAT | 385 |
| Val | Trp | Glu | Gly | Thr | Tyr | Asn | Arg | Ala | Val | Leu | Asp | Asn | Tyr | |
| | 100 | | | | 105 | | | | | 110 | | | | |
| TAT | GCC | AAA | CAG | AAA | ATT | ACC | GTG | GGC | TTG | ACG | GTT | TTT | GCT | 427 |
| Tyr | Ala | Lys | Gln | Lys | Ile | Thr | Val | Gly | Leu | Thr | Val | Phe | Ala | |
| | | 115 | | | | 120 | | | | | 125 | | | |
| GTC | GGA | AGA | TAC | ATT | GAG | CAT | TAC | TTG | GAG | GAG | TTC | TTA | ATA | 469 |
| Val | Gly | Arg | Tyr | Ile | Glu | His | Tyr | Leu | Glu | Glu | Phe | Leu | Ile | |

|     |     |     |     | 130 |     |     |     |     | 135 |     |     |     |     | 140 |     |      |
|-----|-----|-----|-----|-----|-----|-----|-----|-----|-----|-----|-----|-----|-----|-----|-----|------|
| TCT | GCA | AAT | ACA | TAC | TTC | ATG | GTT | GGC | CAC | AAA | GTC | ATC | TTT |     |     | 511  |
| Ser | Ala | Asn | Thr | Tyr | Phe | Met | Val | Gly | His | Lys | Val | Ile | Phe |     |     |      |
|     |     |     | 145 |     |     |     |     |     | 150 |     |     |     |     |     |     |      |
| TAC | ATC | ATG | GTG | GAT | GAT | ATC | TCC | AGG | ATG | CCT | TTG | ATA | GAG |     |     | 553  |
| Tyr | Ile | Met | Val | Asp | Asp | Ile | Ser | Arg | Met | Pro | Leu | Ile | Glu |     |     |      |
| 155 |     |     |     |     | 160 |     |     |     |     | 165 |     |     |     |     |     |      |
| CTG | GGT | CCT | CTG | CGT | TCC | TTT | AAA | GTG | TTT | GAG | ATC | AAG | TCC |     |     | 595  |
| Leu | Gly | Pro | Leu | Arg | Ser | Phe | Lys | Val | Phe | Glu | Ile | Lys | Ser |     |     |      |
|     | 170 |     |     |     |     |     | 175 |     |     |     |     | 180 |     |     |     |      |
| GAG | AAG | AGG | TGG | CAA | GAC | ATC | AGC | ATG | ATG | CGC | ATG | AAG | ACC |     |     | 637  |
| Glu | Lys | Arg | Trp | Gln | Asp | Ile | Ser | Met | Met | Arg | Met | Lys | Thr |     |     |      |
|     |     | 185 |     |     |     |     |     | 190 |     |     |     |     | 195 |     |     |      |
| ATC | GGG | GAG | CAC | ATC | CTG | GCC | CAC | ATC | CAG | CAC | GAG | GTG | GAC |     |     | 679  |
| Ile | Gly | Glu | His | Ile | Leu | Ala | His | Ile | Gln | His | Glu | Val | Asp |     |     |      |
|     |     |     | 200 |     |     |     |     | 205 |     |     |     |     | 210 |     |     |      |
| TTC | CTC | TTC | TGC | ATT | GAC | GTG | GAT | CAG | GTC | TTC | CAA | AAC | AAC |     |     | 721  |
| Phe | Leu | Phe | Cys | Ile | Asp | Val | Asp | Gln | Val | Phe | Gln | Asn | Asn |     |     |      |
|     |     |     |     | 215 |     |     |     |     |     | 220 |     |     |     |     |     |      |
| TTT | GGG | GTG | GAG | ACC | CTG | GGC | CAG | TCG | GTG | GCT | CAG | CTA | CAG |     |     | 763  |
| Phe | Gly | Val | Glu | Thr | Leu | Gly | Gln | Ser | Val | Ala | Gln | Leu | Gln |     |     |      |
| 225 |     |     |     |     | 230 |     |     |     |     | 235 |     |     |     |     |     |      |
| GCC | TGG | TGG | TAC | AAG | GCA | CAT | CCT | GAC | GAG | TTC | ACC | TAC | GAG |     |     | 805  |
| Ala | Trp | Trp | Tyr | Lys | Ala | His | Pro | Asp | Glu | Phe | Thr | Tyr | Glu |     |     |      |
|     | 240 |     |     |     |     | 245 |     |     |     |     | 250 |     |     |     |     |      |
| AGG | CGG | AAG | GAG | TCC | GCA | GCC | TAC | ATT | CCG | TTT | GGC | CAG | GGG |     |     | 847  |
| Arg | Arg | Lys | Glu | Ser | Ala | Ala | Tyr | Ile | Pro | Phe | Gly | Gln | Gly |     |     |      |
|     |     | 255 |     |     |     |     | 260 |     |     |     |     | 265 |     |     |     |      |
| GAT | TTT | TAT | TAC | CAC | GCA | GCC | ATT | TTT | GGG | GGA | ACA | CCC | ACT |     |     | 889  |
| Asp | Phe | Tyr | Tyr | His | Ala | Ala | Ile | Phe | Gly | Gly | Thr | Pro | Thr |     |     |      |
|     |     |     | 270 |     |     |     |     | 275 |     |     |     |     | 280 |     |     |      |
| CAG | GTT | CTA | AAC | ATC | ACT | CAG | GAG | TGC | TTC | AAG | GGA | ATC | CTC |     |     | 931  |
| Gln | Val | Leu | Asn | Ile | Thr | Gln | Glu | Cys | Phe | Lys | Gly | Ile | Leu |     |     |      |
|     |     |     |     | 285 |     |     |     |     | 290 |     |     |     |     |     |     |      |
| CAG | GAC | AAG | GAA | AAT | GAC | ATA | GAA | GCC | GAG | TGG | CAT | GAT | GAA |     |     | 973  |
| Gln | Asp | Lys | Glu | Asn | Asp | Ile | Glu | Ala | Glu | Trp | His | Asp | Glu |     |     |      |
| 295 |     |     |     |     | 300 |     |     |     |     | 305 |     |     |     |     |     |      |
| AGC | CAT | CTA | AAC | AAG | TAT | TTC | CTT | CTC | AAC | AAA | CCC | ACT | AAA |     |     | 1015 |
| Ser | His | Leu | Asn | Lys | Tyr | Phe | Leu | Leu | Asn | Lys | Pro | Thr | Lys |     |     |      |
|     | 310 |     |     |     |     | 315 |     |     |     |     | 320 |     |     |     |     |      |
| ATC | TTA | TCC | CCA | GAA | TAC | TGC | TGG | GAT | TAT | CAT | ATA | GGC | ATG |     |     | 1057 |
| Ile | Leu | Ser | Pro | Glu | Tyr | Cys | Trp | Asp | Tyr | His | Ile | Gly | Met |     |     |      |
|     |     | 325 |     |     |     |     | 330 |     |     |     |     | 335 |     |     |     |      |
| TCT | GTG | GAT | ATT | AGG | ATT | GTC | AAG | ATA | GCT | TGG | CAG | AAA | AAA |     |     | 1099 |
| Ser | Val | Asp | Ile | Arg | Ile | Val | Lys | Ile | Ala | Trp | Gln | Lys | Lys |     |     |      |
|     |     |     | 340 |     |     |     |     | 345 |     |     |     |     | 350 |     |     |      |
| GAG | TAT | AAT | TTG | GTT | AGA | AAT | AAC | ATC | TGACTTTAAA |  |  |  |  |  |  | 1136 |
| Glu | Tyr | Asn | Leu | Val | Arg | Asn | Asn | Ile |     |     |     |     |     |     |     |      |
|     |     |     |     | 355 |     |     |     |     |     |     |     |     |     |     |     |      |

| TTGTGCCAGC | AGTTTTCTGA | ATTTGAAAGA | GTATTACTCT | GGCTACTTCC | 1186 |
| TCAGAGAAGT | AGCACTTAAT | TTTAACTTTT | AAAAAAATAC | TAACAAAATA | 1236 |
| CCAACACAGT | AAGTACATAT | TATTCTTCCT | TGCAACTTTG | AGCCTTGTCA | 1286 |
| AATGGGAGAA | TGACTCTGTA | GTAATCAGAT | GTAAATTCCC | AATGATTTCT | 1336 |
| TATCTGCGGA | ATTCCAGCTG | AGCGCCGGTC | GCTACCATTA | CCAGTTGGTC | 1386 |
| TGGTGTCGAC | GACTCCTGGA | GCCCGTCAGT | ATCGGCG    |            | 1423 |

( 2 ) INFORMATION FOR SEQ ID NO:3:

(  i  ) SEQUENCE CHARACTERISTICS:
            ( A ) LENGTH: 31 bases
            ( B ) TYPE: Nucleic Acid
            ( C ) STRANDEDNESS: Single
            ( D ) TOPOLOGY: Linear (  i  i  ) MOLECULE TYPE: Other Nucleic Acid
            ( A ) DESCRIPTION: PCR primer 'GT- 1

(  x  i  ) SEQUENCE DESCRIPTION: SEQ ID NO:3:

GAATTCAAGC TTATGATCAC TATGCTTCAA G                                   31

( 2 ) INFORMATION FOR SEQ ID NO:4:

(  i  ) SEQUENCE CHARACTERISTICS:
            ( A ) LENGTH: 29 bases
            ( B ) TYPE: Nucleic Acid
            ( C ) STRANDEDNESS: Single
            ( D ) TOPOLOGY: Linear (  i  i  ) MOLECULE TYPE: Other Nucleic Acid
            ( A ) DESCRIPTION: PCR primer 'GT- 2

(  i  i  i  ) HYPOTHETICAL: No (  i  v  ) ANTI-SENSE: Yes (  x  i  ) SEQUENCE DESCRIPTION: SEQ ID NO:4:

GAATTCCTGC AGTCAGACAT TATTCTAAC                                      29